United States Patent [19]
Block et al.

[11] Patent Number: 5,554,185
[45] Date of Patent: Sep. 10, 1996

[54] INFLATABLE PROSTHETIC CARDIOVASCULAR VALVE FOR PERCUTANEOUS TRANSLUMINAL IMPLANTATION OF SAME

[76] Inventors: Peter C. Block, 3510 SW. Sherwood Pl., Portland, Oreg. 97201; W. Earl Anderson, 230 E. 38th Ave., Eugene, Oreg. 97405-4714; David G. Atteridge, 18235 SW. Barcelona Way, Beaverton, Oreg. 97007

[21] Appl. No.: 276,663

[22] Filed: Jul. 18, 1994

[51] Int. Cl.⁶ ..................................................... A61F 2/24
[52] U.S. Cl. ................... 623/2; 623/12; 623/900; 606/195
[58] Field of Search ............................... 623/2, 12, 900; 606/195

[56] References Cited

U.S. PATENT DOCUMENTS

| | | |
|---|---|---|
| 3,671,979 | 6/1972 | Moulopoulos . |
| 4,056,854 | 11/1977 | Boretos et al. . |
| 4,183,102 | 1/1980 | Guiset ......................................... 623/12 |
| 4,592,340 | 6/1986 | Boyles . |
| 4,727,873 | 3/1988 | Mobin-Uddin . |
| 4,817,600 | 4/1989 | Herms et al. . |
| 4,960,424 | 10/1990 | Grooters . |
| 4,994,077 | 2/1991 | Dobben . |
| 5,163,897 | 11/1992 | Persky ......................................... 623/12 |
| 5,163,953 | 11/1992 | Vince . |
| 5,207,695 | 5/1993 | Trout, III . |
| 5,360,444 | 11/1994 | Kusuhara ...................................... 623/2 |
| 5,370,691 | 12/1994 | Samson ........................................ 623/12 |
| 5,397,351 | 3/1995 | Povcnik et al. ............................... 623/2 |

FOREIGN PATENT DOCUMENTS

| | | |
|---|---|---|
| 2700531 | 7/1977 | Germany . |
| 91/17720 | 11/1991 | WIPO . |
| 93/01768 | 2/1993 | WIPO . |

*Primary Examiner*—Paul B. Prebilic
*Attorney, Agent, or Firm*—Stetina Brunda Buyan; Raymond Sun

[57] ABSTRACT

An inflatable prosthetic cardiovascular valve which is constructed so as to be initially deployable in a deflated "collapsed" configuration wherein the valve may be passed through the lumen of a cardiovascular catheter and subsequently inflated to an "operative" configuration so as to perform its intended valving function at its intended site of implantation within the cardiovascular system. The inflated valve may be held in place by mechanical means (e.g., hooks, projections), by chemical adhesive or through biological assimilation by the heart tissue.

17 Claims, 3 Drawing Sheets

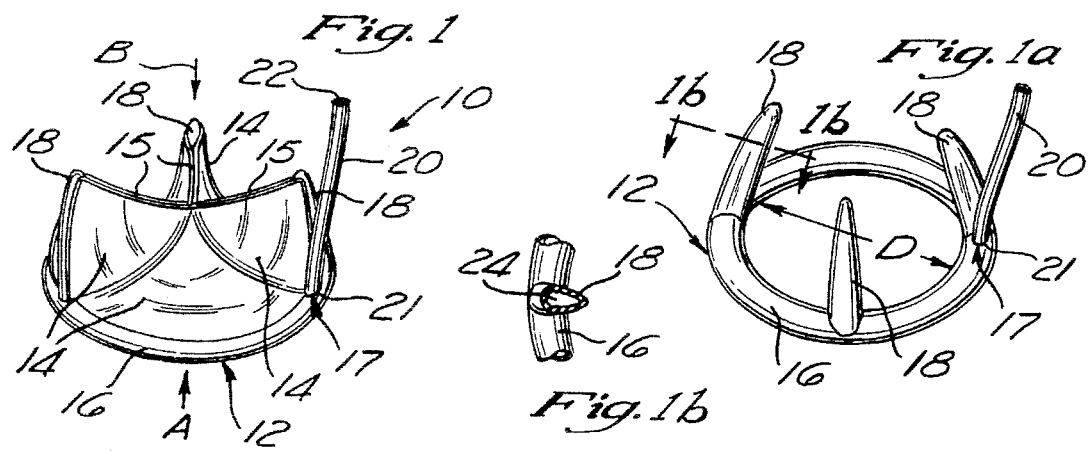
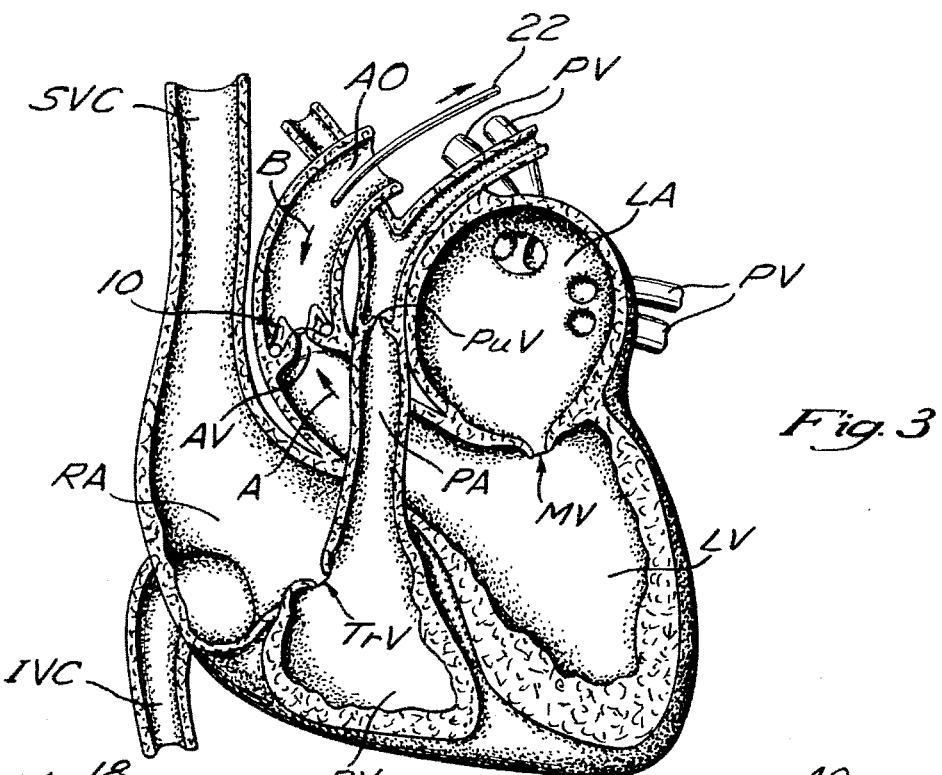
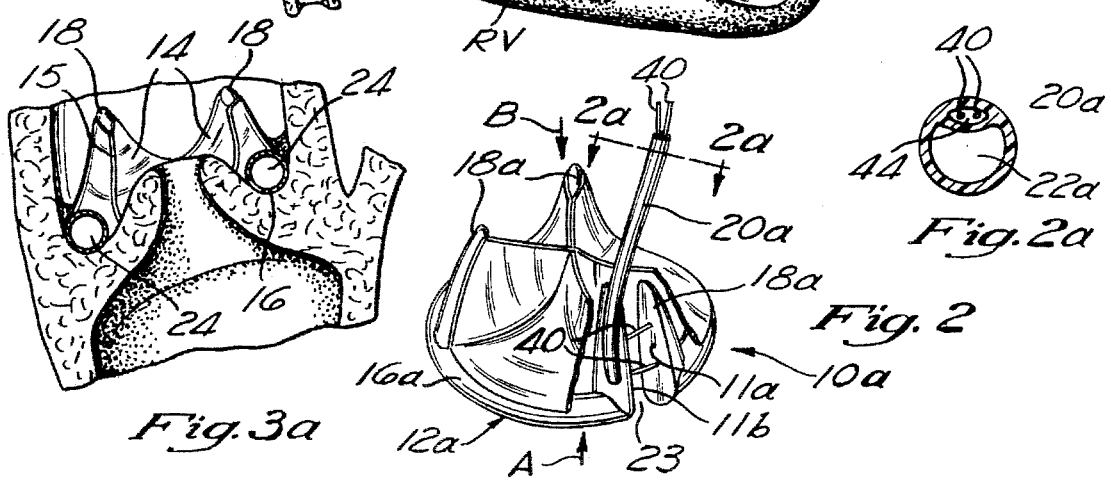

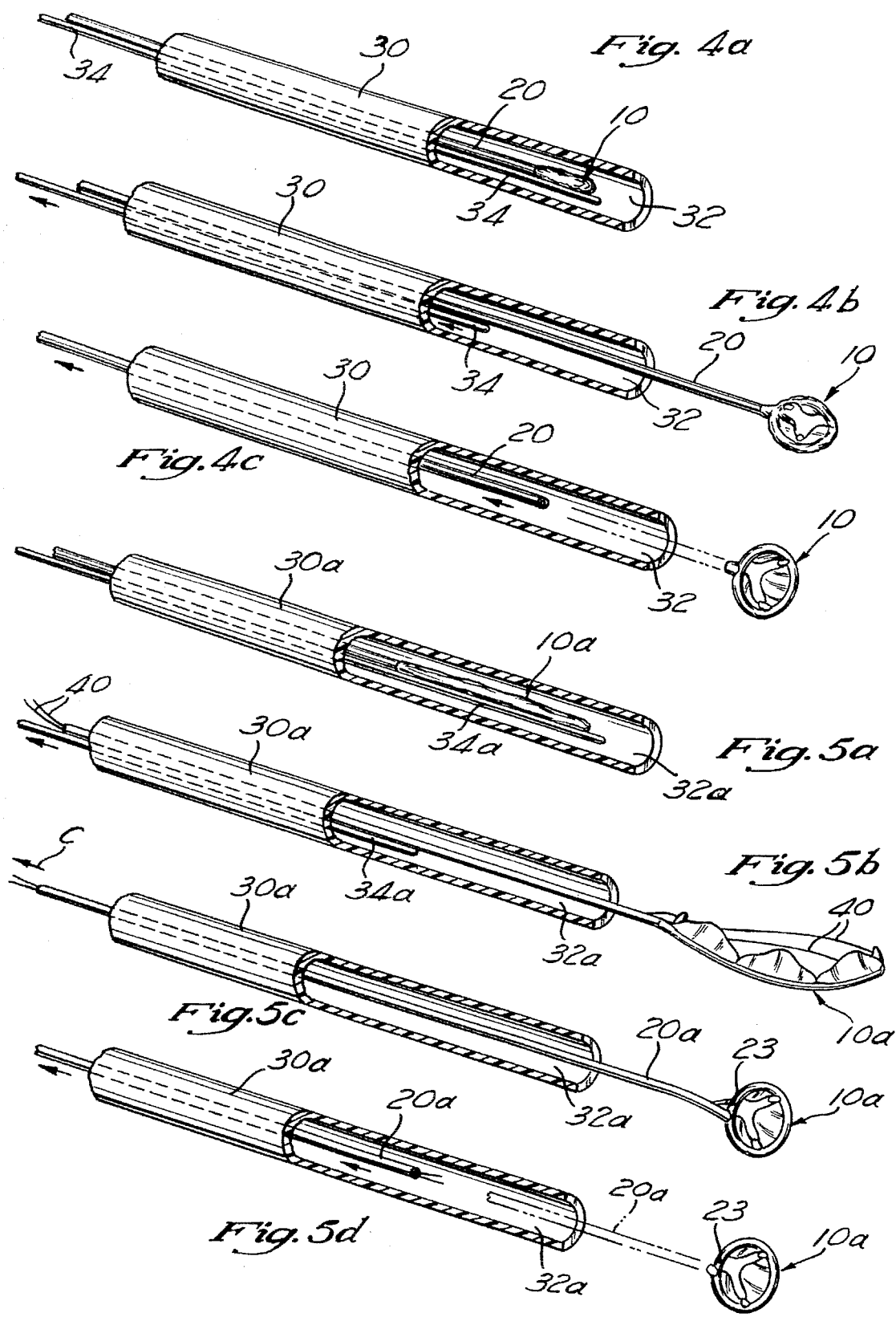

INFLATABLE PROSTHETIC CARDIOVASCULAR VALVE FOR PERCUTANEOUS TRANSLUMINAL IMPLANTATION OF SAME

FIELD OF THE INVENTION

The present invention pertains generally to medical equipment, and more particularly a catheter-introducible prosthetic valve which may be implanted into a mammalian heart or elsewhere in the cardiovascular system to augment or replace a malfunctioning endogenous valve.

BACKGROUND OF THE INVENTION

The prior art has included numerous surgically implantable prosthetic valves which may be utilized to replace malfunctioning heart valves, such as the aortic valve and the mitral valve. Some of the prosthetic heart valves of the prior art are "mechanical" valves of non-biological origin. Others are "biological" valves wherein all or a portion of the valve consists of harvested mammalian (e.g., porcine) tissue which has been preserved by way of a chemical fixation process.

Although surgically implantable prosthetic heart valves have become widely used in clinical practice, their implantation involves a major cardiothoracic surgical procedure wherein the patient must be placed on full cardiopulmonary bypass for a significant period of time. As a result, patients who have severe complications of their valvular disease or who are otherwise severely ill or elderly may be unable to undergo the rigors of such major cardiothoracic surgical procedure and are, thus, unable to receive the benefits of a surgically implanted prosthetic cardiovascular valve.

A number of prior investigators have proposed various "collapsible" cardiovascular valves and other cardiovascular apparatus (e.g., embolus traps) which may be collapsed and inserted into the mammalian vasculature through the lumen of a tubular catheter or introducer. Examples of collapsible cardiovascular valves and related apparatus are found in U.S. Pat. Nos. 3,671,979; 4,056,854; 4,592,340; 4,727,873; 4,817,600; 4,960,424; 4,994,077; 5,163,953; and 5,207,695, as well as the following foreign patents and/or patent publications WO91/17720; DT 2700-531 and WO93/01768.

Although various collapsible, catheter deployable, heart valves and/or other cardiovascular apparatus may have been proposed in the prior art, there remains a need for further refinement and development of such devices so as to arrive at a clinically useful prosthetic cardiovascular valve which may be implanted, through the lumen of a cardiovascular catheter, without the need for major cardiothoracic surgery.

SUMMARY OF THE INVENTION

Broadly stated, the present invention comprises an inflatable prosthetic cardiovascular valve which, when in a deflated state, is sufficiently collapsible to be passed through the lumen of a tubular cardiovascular catheter and which, when subsequently inflated, will assume a fully functional operative cardiovascular valve configuration.

In accordance with a first integral or annular embodiment of the invention, there is provided a collapsible prosthetic cardiovascular valve comprising an annular inflatable toroidal valve body and one or more occluder members (e.g., pliable leaflets) affixed thereto. A plurality of legs or strut members may extend from one side of the toroidal valve body to facilitate attachment of, and/or to maintain operative positioning of, the valve leaflets.

In accordance with a second split or linear embodiment of the invention, there is provided a collapsible prosthetic cardiovascular valve comprising an inflatable valve body having a split or separation formed therein and one or more occluder members (e.g., pliable leaflets) affixed thereto. When deflated, the valve body may be separated at its split or separation and extended into an elongate linear deflated configuration. When inflated, the valve body assumes a function annular or circular configuration. The inflatable valve body may be inherently biased to assume said annular or circular configuration upon inflation thereof, or may be provided with one or more tether lines or other guide members useable to guide or pull the valve body into the desired annular configuration as inflation of the valve body is accomplished.

Although the prosthetic cardiovascular valves of the present invention may incorporate various numbers of individual valve leaflets, a preferred embodiment of the valve incorporates three (3) valve leaflets, each having three (3) inboard edges which meet along a tre-foil margin within the annular central passageway of the inflatable valve body.

Although the collapsible cardiovascular valves of the present invention may be inflated by various means, one preferred embodiment of the invention employs a detachable inflation tube which is initially connected to the valve, and which may be subsequently severed from the valve and removed following inflation thereof.

The inflatable cardiovascular valves of the present invention may be inflated with any suitable inflation fluid. In some embodiments, the valve may be initially inflated with material(s) which will react or otherwise undergo gelation or solidification within the valve body, thereby resulting in a gel-filled or solid-filled valve.

The collapsible cardiovascular valves of the present invention may be specifically sized and configured for implantation at various sites or locations within the cardiovascular anatomy. In particular, collapsible valves of the present invention may be sized or configured to replace or augment any natural heart valve, including the mitral and aortic valves of the human heart. Similarly, collapsible cardiovascular valves of the present invention may be sized and configured for implantation in veins of the extremities to replace or augment absent or malfunctioning venous valves. In instances when the valves of the present invention are utilized to replace or augment the aortic valve of the heart, the positioning and location of the prosthetic valve of the present invention will be such that the prosthetic valve does not interfere with blood flow into the coronary circulation.

Further in accordance with the invention, there are provided apparatus and methods for percutaneous transluminal insertion and utilization of the collapsible/inflatable cardiovascular valves of the above-described character.

Further objects and advantages of the invention will become apparent to those skilled in the art upon reading and understanding of the following detailed description and the accompanying drawings.

BRIEF DESCRIPTION OF THE DRAWINGS

FIG. 1 is a perspective view of a catheter-introducible cardiovascular valve of the present invention having an inflatable toroidal support structure.

FIG. 1a is a perspective view of the inflatable toroidal support structure portion of the catheter-introducible cardiovascular valve of FIG. 1.

FIG. 1b is a cut away plan view of the portion of the inflatable toroidal support structure shown in FIG. 1a.

FIG. 2 is a perspective view of an alternative "split" embodiment of a catheter-introducible prosthetic valve of the present invention.

FIG. 3 is a cross-sectional diagram of a human heart having an inflatable prosthetic valve of the present invention implanted adjacent the endogenous aortic valve.

FIG. 3a is an enlarged view of region AV of FIG. 3.

FIGS. 4a–4c provide a step-by-step diagram of a method by which the prosthetic valve of FIG. 1 may be inserted, inflated and implanted in the body of a human being or other mammal.

FIGS. 5a–5d are a step-by-step diagram of a method by which the prosthetic cardiovascular valve of FIG. 2 may be inserted, inflated and implanted in the body of a human being or other mammal.

DETAILED DESCRIPTION OF PREFERRED EMBODIMENTS

Figure 1C:
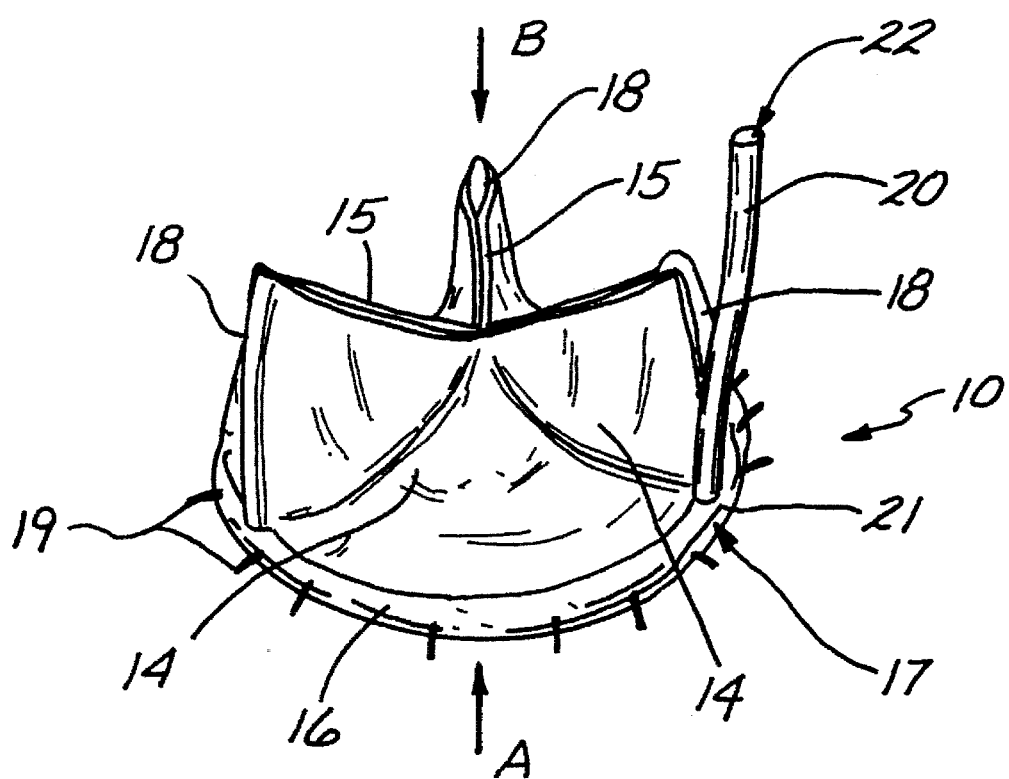
FIG. 1c is a perspective view of the prosthetic valve of FIG. 1 illustrating anchoring members provided thereon.

The detailed description set forth below in connection with the appended drawings is intended merely as a description of the presently preferred embodiments of the invention, and is not intended to represent the only form in which the present invention may be constructed or utilized. The description sets forth the functions and sequence of steps for construction and implementation of the invention in connection with the illustrated embodiments. It is to be understood, however, that the same or equivalent functions and sequences may be accomplished by different embodiments that are also intended to be encompassed within the spirit and scope of the invention.

I. CONSTRUCTION OF INFLATABLE CARDIOVASCULAR VALVES OF THE PRESENT INVENTION

With reference to FIGS. 1, 1a and 1b, there is shown a first embodiment of a prosthetic cardiovascular valve 10 of the present invention comprising an inflatable support body 12 having one or more pliable valve leaflets 14 mounted thereon. The leaflets 14 are configured and constructed so as to move, in response to hemodynamic movement of the blood, between a) an "open" configuration wherein blood may flow through the valve in a first direction A and, b) a "closed" configuration whereby blood is prevented from back flowing through the valve in a second direction B.

In the embodiment shown in FIGS. 1, 1a and 1b, the inflatable stent or support body 12 of the valve 10 comprises an inflatable annular ring or toroid 16 having a plurality of inflatable legs or struts 18 extending therefrom. An inflation tube 20 is initially attached to an inflation port 17 on the inflatable body 12 of the valve 10 to permit infusion of inflation fluid into the inner cavity 24 of the inflatable support body 12. Such inflation tube 20 preferably comprises a pliable, elongate tube having a hollow lumen 22 extending longitudinally therethrough.

The distal end of the inflation tube 20 may be detachable from the inflatable body 12 of valve 10 such that, after the valve 10 has been fully inflated, the inflation tube 20 may be volitionally detached from the valve 10 and subsequently extracted and removed.

In embodiments wherein the inflation tube 20 is detachable from the valve 10, a sealing element 21 such as a check valve or sphincter like elastic ring may be disposed within or adjacent the inflation port 17 or other location where the inflation tube 20 separates or disconnects from the valve 10, so as to result in closure of the inflation port 17 or residual portion of tube lumen 22, thereby preventing leakage or seepage of the inflation material or fluid from the inner cavity 24 of the valve 10.

The valve leaflets 14 may be formed of any material(s) suitable for performing the leaflet function, including thin membranes or sheets of pliable synthetic or biological material capable of flexing back and forth between the above-described "open" and "closed" configurations in response to hemodynamic movement of the blood against the leaflets 14, yet sufficiently resistant to extension that leaflet(s) perform their intended function.

As such, the leaflets 14 are preferably constructed and configured to mimic the function of the leaflets or cusps of a healthy endogenous cardiovascular valve. Synthetic leaflets 14 may be formed of elastomeric materials such as polyurethane, silicone, rubbers, etc. suitably modified to provide limited extensibility. Biological leaflets 14 may be formed of chemically fixed mammalian valvular tissue or other biological tissue (e.g., pericardium) which is sufficiently thin and pliable to perform the desired valving function of the leaflets 14.

Although the leaflets may vary in number and configuration, the presently preferred embodiments shown in the drawings utilize three (3) separate leaflets 14 having correspondingly configured inboard edges 15 which, when in their closed position, interact or meet with one another in a tre-foil margin as shown.

The valve leaflets 14 may be mounted on or attached to the inflatable support body 12 by any suitable means, including suturing or adhesive. For example, in some embodiments the material of which the leaflets 14 are formed may be wrapped around portions of the inflatable body 12 and subsequently sutured in place to hold such biological leaflet material on the inflatable support body 12. In other embodiments wherein biological or synthetic material is employed, it may be desirable to apply quantities of adhesive to affix the leaflets 14 to the inflatable support body 12. Also, in some embodiments, the leaflets 14 may be formed of synthetic material integral with the inflatable support body 12.

The presently preferred embodiments of the invention include an integral or annular embodiment (FIGS. 1 and 1a) as well as a split or linear embodiment (FIGS. 2 and 2a).

In the integral or annular embodiment of the valve 10 (FIGS. 1 and 1a) the inflatable valve support body 12 is in the form of a continuous ring or annulus which, when deflated, may be compressed or compacted into a sufficiently small space to pass through a catheter lumen of approximately 4–7 mm in diameter. Thereafter, the valve support body 12 may be inflated to cause the valve to assume the operative annular or ringlike structure shown in FIG. 1.

In the alternative linear or "split" embodiment of the valve 10a shown in FIG. 2, a division or closed split 23 is formed vertically through one of the strut members 18a, as shown. In such embodiment, the valve 10a may be deflated to a flaccid state and subsequently extended into an elongate outstretched configuration whereby a first end 11a of the split 23 is situated at one longitudinal end of the valve 10a and the opposite or second end 11b of the split 23 is situated at the opposite end of the valve 10a, as illustrated in FIG. 5b.

Optionally, in the "split" embodiment shown in FIG. 2, one or more pull line(s) or tether(s) 40 may be attached to the valve 10a to facilitate movement of the valve 10a from its deflated linearly extended and compact configuration (FIG. 5b) to its generally circular inflated operative configuration (FIG. 5d). The tether(s) 40 may initially extend separately from and alongside the inflation tube 20a or may be contained within one or more tether guides or passageways associated with or formed within the inflation tube 20a. Specifically, in the embodiment shown in FIG. 2, a separate tether guide lumen 44 extends longitudinally through the inflation tube 22a, which is incorporated with the first end member of split support strut 18a, and into that first end strut member 18a where it terminates distally in a tether entry apertures formed in the face of the split portion 11a, opposite the points on corresponding split portion 11b where the distal ends of tethers 40 is connected to the second portion 11b of the split support strut 18a. From this connection, tethers 40 pass into tether entry apertures formed in the corresponding split portion 11b and extend proximally through tether guide lumen 44 of inflation tube 20a. The proximal ends of the tethers 40 emerge out of and/or apart from the proximal end of the inflation tube 20a so as to be grasped and retracted by the operator. As such, retraction of the tethers 40 in the proximal direction (arrow C) will guide or pull the second split portion 11b of the split support strut 18a into juxtaposition with the first split portion 11a thereof.

The connection or attachment of the distal ends of tethers 40 to the second split portion 11b of the split valve support body 12a may be a releasable connection whereby the distal ends of tethers 40 may be released and pulled away from the valve 10a simultaneously or separate from detachment of the inflation tube 22a from the valve body 12a. The releasable or tearable connection of the distal ends of the tethers 40 to the second portion 11b of the split support strut 18a may be specifically constructed such that the amount of tension required to tear or separate the tethers 40 from the valve 10a can only be exerted when the valve 10a is properly anchored in its desired position within the mammalian body.

The valve 10, 10a of the present invention may be implanted at many different desired locations in the mammalian cardiovascular system. For example, the valves 10, 10a may be implanted adjacent to or in replacement of a malfunctioning heart valve, as shown in the illustration of the human heart shown in FIG. 3. The anatomical structure and major blood vessels of the heart are labeled on FIG. 3 in accordance with the following legend:

| | |
|---|---|
| PV | Pulmonary Veins |
| PA | Pulmonary Artery |
| RPA | Right Pulmonary Artery |
| LPA | Left Pulmonary Artery |
| SVC | Superior Vena Cava |
| IVC | Inferior Vena Cava |
| AO | Aorta |
| RA | Right Atrium |
| RV | Right Ventricle |
| LA | Left Atrium |
| LV | Left Ventricle |
| AV | Aortic Valve Position |
| MV | Mitral Valve Position |
| TrV | Tricuspid Valve |
| PuV | Pulmonic Valve |

In embodiments where the valve 10, 10a is implanted in the aortic position on the outflow side of the endogenous aortic valve, (see FIG. 3) it will be appreciated that the valve 10, 10a must be carefully positioned so as not to impede or block bloodflow into the coronary ostia. Additionally, it will be appreciated that the valves 10, 10a of the present invention may be useful in various peripheral, extracardiac locations, such as in the veins of the lower extremities as replacements and/or augmentations for absent or malfunctioning endogenous venous valves.

II. INFLATION OF THE CARDIOVASCULAR VALVES OF THE PRESENT INVENTION

The inflatable cardiovascular valve 10, and in particular the inflatable support body 12 of the valve 10 may be inflated by any suitable inflation fluid or substance.

In some embodiments and applications, it may be desirable to inflate the support body 12 with a gas or liquid (e.g., carbon dioxide or saline solution) which may subsequently be extracted or removed from the valve body 12 if it is subsequently desired to deflate the valve 10.

In other embodiments and applications, it may be desirable to inflate the valve 10 with a fluid which subsequently gels or solidifies within the inflation space 24 of the valve support body 12, thereby minimizing any likelihood that the inflation substance would inadvertently leak or seep from the implanted valve 10. For example, one or two component elastomer-forming chemical reactants may be initially instilled into the inflation space 24 of the support body 12 through inflation tube 20 while in a liquid state, and subsequently allowed to gel or solidify within the inflation space 24 of the valve support body 12 so as to result in a gelatinous or solidified (e.g., elastomeric or rigid) filling material within the inflation space 24 of the inflated valve 10.

In embodiments wherein the valve 10 is inflated with flowable liquid or gaseous inflation fluid(s), it may be possible to subsequently deflate and remove the valve, while in embodiments wherein gelling or solidifying inflation materials are employed, subsequent deflation and removal of the valve may be rendered non-feasible. Accordingly, the selection of the type of inflation material to be employed may depend on whether it is desirable to subsequently deflate the valve.

Alternatively, a two stage inflation technique may be utilized whereby an initial temporary liquid or gaseous inflation fluid is initially utilized to inflate the valve, but is subsequently replaced by a more permanent solidifying or gelling inflation substance. This two-staged inflation technique would permit the valve to be deflated and/or manipulated as needed during the implantation and affixation processes, but would subsequently allow the valve to become permanently inflated and configured after the proper positioning and affixation of the valve has been achieved. In accordance with this aspect of the invention, a bioacceptable or biologically inert temporary inflation fluid (e.g., 0.9 percent NaCl solution) may be initially passed into the valve 10 to effect inflation thereof. After the valve 10 has been appropriately positioned and affixed in its desired operative location, an escape opening may be formed in the body of the valve by puncture thereof, or by other suitable means, and a more permanent inflation substance, such as a material which will subsequently gel or solidify, may be passed into the valve 10, thereby displacing the temporary inflation fluid out of the escape aperture, and allowing the valve to become filled with a more permanent non-escaping inflation material.

III. INSERTION AND POSITIONING OF THE INFLATABLE VALVES OF THE PRESENT INVENTION

The inflatable cardiovascular valve 10 of the present invention may be inserted, deployed and implanted at their intended anatomical locations, by any suitable means.

a) A Preferred Method of Implanting an Annular Inflatable Valve of the First Embodiment FIGS. 4a–4c provide a stepwise illustration of a presently preferred method for percutaneous transluminal catheter introduction of the "integral" or annular first embodiment of the inflatable valve 10 of the present invention.

As shown, a tubular cardiovascular guiding catheter 30 having a hollow lumen 32 extending longitudinally therethrough is initially inserted, by a standard percutaneous introduction technique, into a blood vessel (e.g., the femoral artery). The catheter 30 is advanced through the vasculature until the distal tip of the catheter 30 is positioned adjacent the intended site for implantation of the valve 10.

The valve 10 is initially deployed in its deflated compact configuration and is mounted or attached on an introducer member 34, such as a bendable cardiovascular guidewire or elongate tubular member having an annular slot near the distal end to hold or accommodate the deflated valve 10 therein. The elongate inflation tube 20 attached to the deflated valve 10 is deployed within or alongside the introducer member 34. The introducer member 34 having the deflated valve 10 mounted thereon is then inserted into and advanced through the lumen 32 of the pre-positioned guide catheter 30.

After the distal end of the introducer member 34 having the deflated valve 10 mounted thereon has emerged from the distal luminal opening of the guide catheter 30, a quantity of inflation fluid is injected or infused through the inflation tube 20 and into the inflatable body 12 of the valve 10. The inflating valve 10 is, by virtue of its inflation or by other mechanical or manipulative means, separated from the introducer member 34, thereby allowing the introducer member 34 to be proximally retracted and removed as shown in FIG. 4b.

After the valve 10 has been fully inflated, the inflation tube 20 may be detached, proximally retracted and removed, as shown in FIG. 4c.

The inflated, operatively configured valve 10 (FIG. 4c) may subsequently be held in its desired position within the heart or blood vessel by way of engagement members (for example, pins 19 shown in FIG. 1c, hooks, or other conventional engagement mechanisms) protruding from the valve 10 or by application of one or more physiologically compatible adhesives (e.g., polyurethane adhesive).

In other embodiments and applications, surfaces of valve 10 which contact the receptive body may be provided with, coated, or infused with a suitable biologic element (e.g., a biologically compatible tissue graft or cellular matter obtained from an autologous or otherwise genetically compatible source) such that the aforementioned surfaces on valve 10 will become biologically assimilated within the local tissue and thereby fix the valve 10 as an implant.

After the inflated valve 10 has been adhesively, mechanically or frictionally engaged in its desired implanted location, the catheter 30 may be removed, thereby leaving the inflated, operatively configured valve 10 in its desired implanted position within the heart or vasculature.

b.) A Preferred Method of Implanting a Linear Inflatable Valve of the Second Embodiment The linear inflatable valve 10a of the second embodiment of the present invention may be implanted by the transluminal catheter implantation technique illustrated in FIGS. 5a–5d.

As shown, an elongate guide catheter 30a having a hollow lumen 32a extending longitudinally therethrough is initially inserted into the vasculature by a known percutaneous insertion technique and is subsequently advanced to a position whereat the distal tip of the catheter 30a is positioned adjacent the intended site of implantation of the valve 10a.

The deflated, linearly extended, valve 10a is initially mounted on or in an introducer member 34a, such as a pliable cardiovascular guidewire or elongate tube having a linear slot for receiving and/or accommodating all or a portion of the deflated valve 10a.

The inflation tube 20a and optional manipulation tether 40 may be initially extended alongside the introducer 34a.

The introducer 34a having the deflated, linearly extended, valve 10a positioned thereon is then inserted into the lumen 32a of the pre-positioned guide catheter 30a and advanced therethrough until the distal end of the introducer 34a having the deflated valve 10a mounted thereon has emerged from the distal opening of the guide catheter lumen 32a.

Inflation fluid is then passed through inflation tube 20a and into the valve 10a. The act of inflation of the valve 10a, and/or other physical manipulation means, is employed to separate the valve 10a from the introducer 34a, thereby permitting the introducer 34a to be proximally extracted and removed as shown in FIG. 5b.

As the valve 5b is being inflated, the manipulation tethers 40 may be pulled or otherwise manipulated by the operator so as to draw the distal or second end 11a of the linearly extended valve into juxtaposition with the proximal or first end 11b thereof. After having been placed in juxtaposition, the opposing surfaces of split 23 are held, affixed or locked together in the closure process, thereby creating the desired annular configuration of the inflated valve.

After the valve 10a has been fully inflated, the inflation tube 20a and the optional manipulation tethers 40 may be detached, proximally withdrawn and removed as shown in FIG. 5d.

The inflated valve 10a may be affixed in its desired position by way of mechanical fixation apparatus (e.g., pins, hooks, etc. . . . ) or adhesive as described above with respect to the valve 10 constructed in accordance with the first embodiment.

After the inflated valve 10a has been adequately affixed in its intended operative location, the guide catheter 30a may be withdrawn and removed, thereby leaving the inflated operatively configured valve 10a at its desired site of implantation within the heart or vasculature.

Although the invention has been described herein with specific reference to presently preferred embodiments thereof, it will be appreciated by those skilled in the art that various additions, modifications, deletions and alterations may be made to such preferred embodiments without departing from the spirit and scope of the invention. Accordingly, it is intended that all reasonably foreseeable additions, deletions, alterations and modifications be included within the scope of the invention as defined in the following claims.

What is claimed is:

1. An inflatable cardiovascular valve initially deployable in a collapsed deflated configuration and subsequently inflatable to a non-collapsed operative configuration, said valve comprising:

a) an inflatable valve support body which, when fully inflated, comprises a generally annular ring defining a central passageway through which blood may flow;

b) at least one leaflet occluder attached to said inflatable valve support body and configured to move back and forth between:
  i. an open position wherein blood may flow in a first direction through said central passageway; and
  ii. a closed position whereby blood is prevented from backflowinq through said central passageway in a second direction, said second direction being opposite said first direction;
c) an inflation port formed on said inflatable valve support body to facilitate inflation thereof; and
d) at least one pin protruding outwardly from said valve and configured to engage said adjacent anatomical structure when said inflatable valve body is inflated.

2. The prosthetic cardiovascular valve of claim 1 wherein said at least one pin member comprises:
  a series of pin members positioned around said annular ring so as to penetrate and engage surrounding anatomical tissue when said valve is inflated.

3. An inflatable cardiovascular valve initially deployable in a collapsed deflated configuration and subsequently inflatable to a non-collapsed operative configuration, said valve comprising:
a) an inflatable valve support body which, when fully inflated, comprises a generally annular ring defining a central passageway through which blood may flow;
b) at least one leaflet occluder attached to said inflatable valve support body and configured to move back and forth between:
  i. an open position wherein blood may flow in a first direction through said central passageway; and
  ii. a closed position whereby blood is prevented from backflowing through said central passageway in a second direction, said second direction being opposite said first direction;
c) an inflation port formed on said inflatable valve support body to facilitate inflation thereof; and
d) a gelatinous inflation substance disposed within said inflatable valve body in sufficient quantity to maintain said valve body in said inflated operative configuration.

4. An inflatable cardiovascular valve initially deployable in a collapsed deflated configuration and subsequently inflatable to a non-collapsed operative configuration, said valve comprising:
a) an inflatable valve support body which, when fully inflated, comprises a generally annular ring defining central passageway through which blood may flow;
b) at least one leaflet occluder attached to said inflatable valve support body and configured to move back and forth between:
  i. an open position wherein blood may flow in a first direction through said central passageway; and
  ii. a closed position whereby blood is prevented from backflowing through said central passageway in a second directions, said second direction being opposite said first direction;
c) an inflation port formed on said inflatable valve support body to facilitate inflation thereof; and
d) a solidified inflation substance disposed within said inflatable valve body to maintain said valve body in said inflated operative configuration.

5. The prosthetic cardiovascular valve of claim 4 wherein said solidified inflation substance is formed within said inflatable valve body by the process comprising the steps of:
  providing at least one solidifying fluid which will form said solidified substance;
  passing said solidifying fluid into said inflatable valve body so as to cause inflation of said valve body and subsequently allowing said at least one fluid to solidify within said valve body.

6. An inflatable cardiovascular valve initially deployable in a collapsed deflated configuration and subsequently inflatable to a non-collapsed operative configuration, said valve adapted for permanent implantation in a patient, said valve comprising:
a) an inflatable valve support body which, when fully inflated, comprises a generally annular ring comprising a first side and a second side, said annular ring defining a central passageway through which blood may flow;
b) at least one leaflet occluder attached to said inflatable valve support body and configured to move back and forth between:
  i. an open position wherein blood may flow in a first direction through said central passageway; and
  ii. a closed position whereby blood is prevented from backflowing through said central passageway in a second direction, said second direction being opposite said first direction;
c) an inflation port formed on said inflatable valve support body to facilitate inflation thereof; and
d) a plurality of strut members extending from one of said sides of said inflated ring member.

7. The prosthetic cardiovascular valve of claim 6 wherein said strut members are inflatable along with said ring member and wherein each said strut member defines a hollow inflation space therewithin consistent with the inflation space defined within said ring member.

8. The prosthetic cardiovascular valve of claim 6 further comprising at least one anchoring member formed on said valve and configured to engage an adjacent anatomical structure when said valve is inflated.

9. The prosthetic cardiovascular valve of claim 6 further comprising a check valve apparatus associated with said inflation port to prevent leakage of inflation fluid out of said inflation port after said valve has been inflated.

10. The prosthetic cardiovascular valve of claim 6 further comprising an elongate inflation tube connected to said inflation port to facilitate inflation of said inflatable valve body.

11. The prosthetic cardiovascular valve of claim 10 wherein said elongate inflation tube is detachably connected to said inflation port such that said inflation tube may be detached from said valve body and removed after said valve body has been inflated.

12. The prosthetic cardiovascular valve of claim 11 further in combination with a check valve apparatus which is operative to prevent the backflow of inflation fluid out of said inflation port after said detachable inflation tube has been detached therefrom.

13. The prosthetic cardiovascular valve of claim 6 wherein said inflatable valve support body and said at least one leaflet occluder are configured and constructed such that, when said valve is in the deflated, collapsed configuration, said valve will be sufficiently compact to be passable through a catheter lumen of approximately 4–7 mm in diameter.

14. The prosthetic cardiovascular valve of claim 6 further in combination with a quantity of inflation fluid disposed within said inflatable valve body to maintain said valve body in said inflated operative configuration.

15. The prosthetic cardiovascular valve of claim 6 wherein said inflatable valve body comprises a continuous inflatable annular ring.

16. The prosthetic cardiovascular valve of claim 6 wherein said inflatable valve body comprises a split inflatable annular ring comprising separated first and second ends such that when said valve body is deflated, said valve body is extendable into a linearly extended configuration and which, when inflated, is configurable in a generally round, annular configuration.

17. An inflatable cardiovascular valve initially deployable in a collapsed deflated configuration and subsequently inflatable to a non-collapsed operative configuration, said valve comprising:
 a) an inflatable valve support body which, when fully inflated, comprises a generally annular ring defining a central passageway through which blood may flow, and wherein said inflatable valve support body comprises separated first and second ends such that when said valve body is deflated, said valve body is extendable into a linearly extended configuration and which, when inflated, is configurable in a generally round, annular configuration;
 b) at least one leaflet occluder attached to said inflatable valve support body and configured to move back and forth between:
  i. an open position wherein blood may flow in a first direction through said central passageway; and
  ii. a closed position whereby blood is prevented from backflowing through said central passageway in a second direction, said second direction being opposite said first direction; and,
 c) an inflation port formed on said inflatable valve support body to facilitate inflation thereof.

\* \* \* \* \*